(12) United States Patent
Jin et al.

(10) Patent No.: US 9,238,614 B1
(45) Date of Patent: Jan. 19, 2016

(54) FULLERENE DERIVATIVE AND METHOD FOR MANUFACTURING A FULLERENE DERIVATIVE

(71) Applicants: SHOWA DENKO K.K., Tokyo (JP); Tohoku University, Miyagi (JP)

(72) Inventors: Tienan Jin, Miyagi (JP); Weili Si, Miyagi (JP); Yoshinori Yamamoto, Miyagi (JP); Takeshi Igarashi, Tokyo (JP)

(73) Assignees: SHOWA DENKO K.K., Tokyo (JP); Tohoku University, Miyagi (JP)

( * ) Notice: Subject to any disclaimer, the term of this patent is extended or adjusted under 35 U.S.C. 154(b) by 0 days.

(21) Appl. No.: 14/315,460

(22) Filed: Jun. 26, 2014

(51) Int. Cl.
*C07C 69/78* (2006.01)
*C07C 67/333* (2006.01)
*C07D 333/24* (2006.01)
*C07C 69/92* (2006.01)

(52) U.S. Cl.
CPC ............... *C07C 69/78* (2013.01); *C07C 67/333* (2013.01); *C07C 69/92* (2013.01); *C07D 333/24* (2013.01)

(58) Field of Classification Search
CPC ....................................................... C07C 69/78
USPC .......................................................... 549/59
See application file for complete search history.

(56) References Cited

PUBLICATIONS

Y. Matsuo et al., "1-Aryl-4-Silylmethyl[60]fullerenes: Synthesis, Properties, and Photovoltaic Performance", Chem. Asian J. 2013, 8, pp. 121-128.
K. Moriwaki et al., "Synthesis and properties of novel methanofullerenes having ethylthienyl and/or n-pentyl group for photovoltaic cells", Tetrahedron 66, 2010, pp. 7316-7321.
S. Lu et al., "Highly Efficient Cu(OAc)2-Catalyzed Dimerization of Monofunctionalized Hydrofullerenes Leading to Single-Bonded [60]Fullerene Dimers", Angew. Chem. Int. Ed. 2012, 51, pp. 802-806.

*Primary Examiner* — Taofiq A Solola
(74) *Attorney, Agent, or Firm* — IPUSA, PLLC

(57) ABSTRACT

Disclosed is a fullerene derivative represented by the following formula (1):

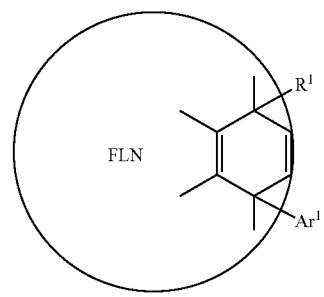

(1)

wherein FLN is a fullerene backbone, $R^1$ is a substituted or non-substituted alkyl group with a carbon number less than or equal to 24, and $Ar^1$ is a substituted or non-substituted aryl group with a carbon number less than or equal to 24.

19 Claims, No Drawings

FULLERENE DERIVATIVE AND METHOD FOR MANUFACTURING A FULLERENE DERIVATIVE

STATEMENT REGARDING PRIOR DISCLOSURES BY THE INVENTOR OR A JOINT INVENTOR

The inventor or a joint inventor made a public disclosure relating to the invention: a presentation "Regioselective synthesis of 1,4-bisfunctionalized fullerenes via NBS-promoted oxidation of fullerene monoradical", 94th Spring Annual Meeting of the Chemical Society of Japan on Mar. 27, 2014, and a corresponding abstract on Mar. 12, 2014.

BACKGROUND OF THE INVENTION

1. Field of the Invention

An aspect of the present invention relates to at least one of a fullerene derivative and a method for manufacturing a fullerene derivative.

2. Description of the Related Art

A fullerene discovered in 1985 is a third allotrope of carbon wherein 60 or more carbon atoms are bonded spherically. Attention is being paid to a fullerene represented by $C_{60}$ or $C_{70}$ as a new functional material for an electronic component, a drug, a cosmetic, or the like, due to its specific molecular shape.

For a method for synthesizing a fullerene, an arc discharge method, a resistance heating method, a laser evaporation method, a combustion method, a thermal decomposition method, and the like have been known, and soot that contains a fullerene is produced in any of the above manufacturing methods. A fullerene soluble in an organic solvent, such as $C_{60}$, $C_{70}$, $C_{76}$, $C_{78}$, $C_{82}$, or $C_{84}$ is obtained by subjecting such soot to extraction with an organic solvent. Furthermore, it is possible to modify such a fullerene chemically to improve its solubility in an organic solvent or water.

One of promising applications of a fullerene is an organic photoelectric conversion element, such as an organic thin film solar cell or an organic photosensor, and in particular, an organic thin film that is formed in a coating process is actively being studied and developed because it is expected that its production cost is low. [6,6]-phenyl-$C_{61}$-butyric acid methyl ester (that may be referred to as "[60]PCBM" below) is a representative electron acceptor material soluble in an organic solvent and is frequently used for such applications.

However, in a case where [60]PCBM is combined with an electron donor material such as poly(3-hexylthiophene) to fabricate an organic thin film solar cell, there are problems that it is not possible to provide a sufficiently high open circuit voltage ($V_{oc}$) because a LUMO level of [60]PCBM is comparatively low and it is not possible to provide a sufficiently high value of short circuit current ($J_{sc}$) because a molar absorption coefficient of [60]PCBM in a visible light region is comparatively small.

In recent years, attention is being paid to a fullerene derivative with a substituent introduced at 1,4-positions of a fullerene backbone (that may be referred to as a "1,4-adduct") as a fullerene derivative capable of solving such problems. In general, a 1,4-adduct is such that extension of a π-electron system on a fullerene backbone is smaller than that of a 1,2-adduct such as [60]PCBM and accordingly its LUMO level is comparatively high, so that it is possible to expect an increase in its open circuit voltage (Voc). Furthermore, a 1,4-adduct has a characteristic absorption peak near 450 nm in a visible light region, so that it is also possible to expect an increase in a short circuit current ($J_{sc}$).

In general, as an alkyl group is introduced to a fullerene backbone, its solubility in an organic solvent is improved to increase its compatibility to a coating process. However, an alkyl group is consequently disadvantageous for controlling a LUMO level of a fullerene derivative, because it is difficult to provide a considerable influence on an electronic state of a fullerene backbone. On the other hand, as an aryl group is directly introduced to a fullerene backbone, it is possible to control a LUMO level of a fullerene derivative comparatively easily because it is possible for an electronic state of an aryl group to provide a significant influence on an electronic state of a fullerene backbone although an effect of improving its solubility in an organic solvent is small due to its rigidity. Hence, it is possible to expect that a 1,4-adduct substituted with an alkyl group and an aryl group at a 1-position and a 4-position of a fullerene backbone respectively is a fullerene derivative material with a high solubility and a facilitated control of an electronic state and is excellent as an acceptor material for a photoelectric conversion element, but a practical example of synthesizing such a material is limited.

In Y. Matsuo et al., Chem. Asian J. 8, 121-128 (2013), a fullerene derivative substituted with an aryl group and a silylmethyl group at a 1-position and a 4-position of $C_{60}$ respectively is synthesized. A synthesis method in Y. Matsuo et al., Chem. Asian J. 8, 121-128 (2013) is a method such that C60 is first reacted with an aryl Grignard reagent, subsequently treated with water to obtain a hydroarylated body as an intermediate and further with a strong alkali to eliminate a hydrogen atom therefrom and thereby produce a fullerene anion, and it is reacted with an alkyl halide group to obtain a target substance. However, this method has a problem that the kind of a substituent capable of being introduced to an alkyl group or an aryl group is limited because a Grignard reagent, a strong alkali, and the like are used. In Y. Matsuo et al., Chem. Asian J. 8, 121-128 (2013), only a fullerene derivative having a substituent could be synthesized wherein the substituent is an alkoxy group, an alkylamino group, an alkyl halide group, or a silyl group.

On the other hand, it becomes clear that a phase separation structure of a current mainstream bulk-hetero-junction-type photoelectric conversion element influences a performance of the element. For a factor influencing a phase separation structure, it is possible to provide a solubility of a material to be used, a compatibility among materials, a solvent to be used for coating, a thermal annealing condition, or the like, and a substituent on a fullerene derivative is important because a solubility or a compatibility with a donor material is significantly influenced thereby. For a representative example of a substituent of a fullerene derivative for influencing a characteristic of a photoelectric conversion element, it is possible to provide an ester structure (an oxycarbonyl group or a carbonyloxy group) for [60]PCBM. K. Moriwaki at al., Tetrahedron 66, 7316-7321 (2010) describes that solubilities of fullerene derivatives with no ester structure, similar to [60]PCBM, in an organic solvent are lower than that of [60]PCBM and characteristics of photoelectric conversion elements using these derivatives are different from one another, and accordingly, suggests that presence or absence of an ester structure in a fullerene derivative influences a phase separation structure for a bulk hetero-junction structure. As described above, a fullerene derivative with an introduced substituent that contains an ester structure is important for controlling a phase separation structure for a bulk hetero-junction structure.

However, as described above, it is not possible for a synthesis method described in Y. Matsuo et al., Chem. Asian J. 8, 121-128 (2013) to synthesize a fullerene derivative having a highly reactive substituent that contains an ester structure. That is, it has not been possible to realize synthesis of a 1,4-adduct that is substituted with an alkyl group for ensuring a solubility in an organic solvent and an aryl group for facilitating a control of a LUMO level and further contains an ester structure in a portion of those groups to control a phase separation structure appropriately.

SUMMARY OF THE INVENTION

According to one aspect of the present invention, there is provided a fullerene derivative represented by the following formula (1):

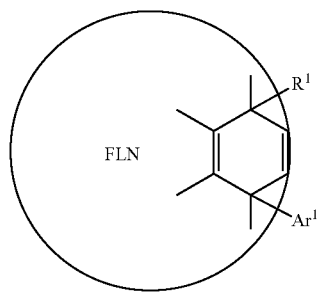

wherein FLN is a fullerene backbone, $R^1$ is a substituted or non-substituted alkyl group with a carbon number less than or equal to 24, and $Ar^1$ is a substituted or non-substituted aryl group with a carbon number less than or equal to 24.

According to another aspect of the present invention, there is provided a method for manufacturing a fullerene derivative, including a step of reacting a fullerene dimer represented by the following formula (2):

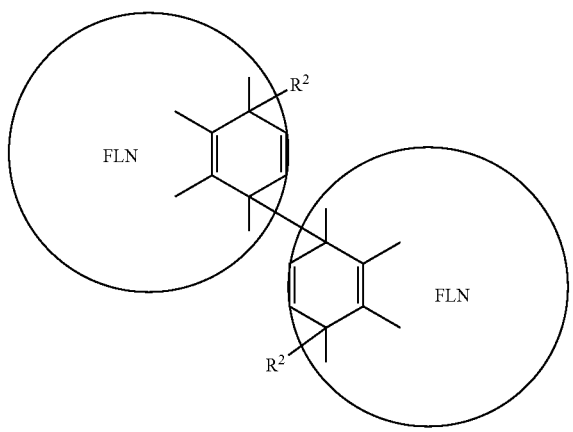

wherein FLN is a fullerene backbone and $R^2$ is a substituted or non-substituted alkyl group with a carbon number less than or equal to 24, with an aromatic compound represented by the following formula (3):

wherein $Ar^2$ is a substituted or non-substituted aryl group with a carbon number less than or equal to 24, under presence of an alcohol and a halogenating agent.

DETAILED DESCRIPTION OF THE PREFERRED EMBODIMENTS

An embodiment of the present invention will be described below.

[Fullerene Derivative]

A fullerene derivative according to an embodiment of the present invention is represented by the following general formula (1):

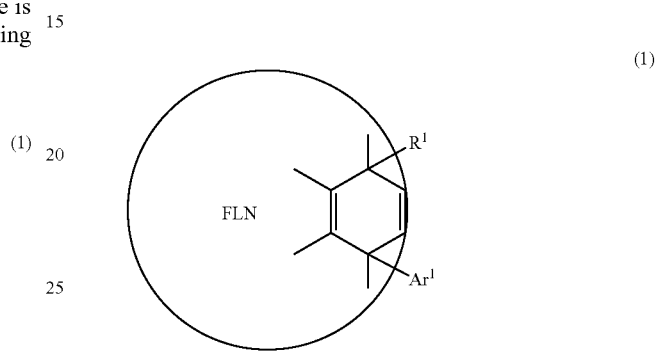

In formula (1) described above, FLN represents a fullerene backbone, $R^1$ represents a substituted or non-substituted alkyl group with a carbon number less than or equal to 24, and $Ar^1$ represents a substituted or non-substituted aryl group with a carbon number less than or equal to 24. Here, the aryl group may be a heteroaryl group. Furthermore, it is preferable for at least one of $R^1$ and $Ar^1$ to contain an ester structure (an oxycarbonyl group or a carbonyloxy group).

Here, a "fullerene derivative" in an embodiment of the present invention refers to a compound having a structure in such a manner that a particular group is added to such a fullerene backbone thereof, and a "fullerene backbone" refers to a carbon backbone that composes a closed-shell structure of a fullerene.

Furthermore, a fullerene derivative according to an embodiment of the present invention is such that an alkyl group and an aryl group are directly added to a fullerene backbone thereof to have a structure represented by general formula (1), and accordingly, has a characteristic such that a control of a solubility in each kind of solvent and an electronic state is facilitated.

Furthermore, in a case where at least one of $R^1$ and $Ar^1$ has an ester structure, a fullerene derivative according to an embodiment of the present invention is readily dissolved in a solvent. Accordingly, it is possible to be used for an application that uses its solution to form a thin film, for example, an organic thin film device material, a resist material, or a surface coating material such as a paint, more preferably than a conventional fullerene derivative.

$R^1$ is a substituted or non-substituted alkyl group and the number of a carbon atom(s) therein is less than or equal to 24. In a case where the number of carbon atoms is greater than 24, a group bonding to a fullerene backbone may be so bulky that it is difficult to be added to the fullerene backbone. Among them, it is preferable for the number of carbon atoms to be 2 to 18, and it is more preferable to be 4 to 18. In a case where the number of carbon atoms is in the range as described above, it is possible to provide an advantageous effect of ensuring a solubility and preventing degradation of a characteristic originating from a fullerene backbone.

Furthermore, in a case where an alkyl group has a substituent, such a substituent is not particularly limited, and it is possible to provide, for example, an aryl group such as a phenyl group or a naphthyl group, an alkoxy group such as a methoxy group, an ethoxy group, or a butoxy group, an ester-structure-containing group such as a methyloxycarbonyl group or an acetyloxy group, a substituted or non-substituted amino group such as a dimethylamino group, an alkenyl group such as a vinyl group, an alkynyl group, or a halogen atom.

Among them, a substituent containing an ester structure is preferable and is excellent in providing a high solubility in an organic solvent.

For a specific example of a substituted or non-substituted alkyl group used as $R^1$, it is possible to provide a straight-chain or branched-chain alkyl group such as a methyl group, an ethyl group, a propyl group, or an isopropyl group, a cyclic alkyl group such as a cyclopropyl group, a cyclopentyl group, or a cyclohexyl group, an aralkyl group such as a benzyl group, or the like.

Among them, an aralkyl group such as a benzyl group is preferable, and is excellent in providing a particularly high solubility in an aromatic solvent that is frequently used in a process for manufacturing an organic thin film device or the like.

Furthermore, a substituted or non-substituted aryl with a carbon number less than or equal to 24 used as $Ar^1$ is not particularly limited, and it is possible to use, for example, a phenyl group or a heteroaryl group such as a pyridyl group, a pyrrolyl group, a 2-furyl group, a 2-thienyl group, or a bithienyl group.

Among them, a phenyl group, a 2-thienyl group, or a bithienyl group is preferable, and a phenyl group is more preferable. In a case where an aryl group is a phenyl group, it is possible to readily introduce a variety of substituents and be excellent in providing many options for controlling an electronic state of a fullerene derivative.

Furthermore, in a case where an aryl group has a substituent, such a substituent is not particularly limited and it is possible to be selected appropriately so that a solubility and an electronic state of a fullerene derivative is controlled, wherein it is possible to provide, for example, an alkyl group such as a methyl group, an ethyl group, or a butyl group, an aryl group such as a phenyl group or a naphthyl group, an alkoxy group such as a methoxy group, an ethoxy group, or a butoxy group, an ester-structure-containing group such as a methyloxycarbonyl group or an acetyloxy group, a substituted or non-substituted amino group such as a dimethylamino group, an alkenyl group such as a vinyl group, an alkynyl group, or a halogen atom.

For a fullerene derivative according to an embodiment of the present invention, it is usually possible to use a fullerene backbone with a carbon number of 60 to 200. For a specific example thereof, it is possible to provide $C_{60}$, $C_{70}$, $C_{76}$, $C_{78}$, $C_{82}$, $C_{84}$, $C_{90}$, $C_{94}$, $C_{96}$, $C_{120}$, $C_{200}$, or the like. Among them, it is preferable for a carbon number of a fullerene backbone to be 60 or 70, and $C_{60}$ is more preferable. This is because it is possible for a smaller carbon number to readily obtain a high purity, and in particular, it is also possible for $C_{60}$ to readily obtain a higher purity than that of another fullerene backbone.

[Method for Manufacturing a Fullerene Derivative]

A method for manufacturing a fullerene derivative according to an embodiment of the present invention is such that a fullerene derivative dimer represented by the following formula (2):

(2)

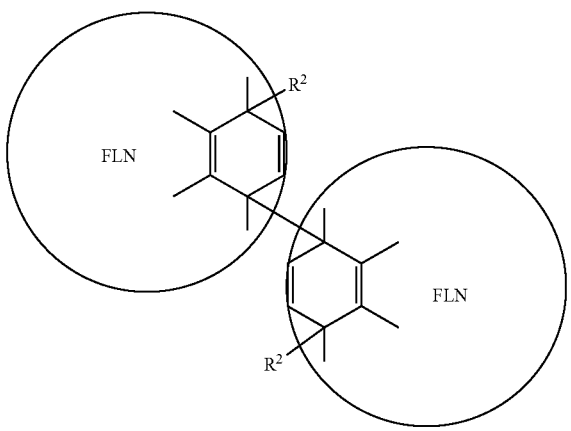

is reacted with an aromatic compound represented by the following formula (3):

$$H—Ar^2 \quad (3)$$

under presence of an alcohol and a halogenating agent to obtain a fullerene derivative represented by the aforementioned formula (1).

In formula (2) described above, FLN represents a fullerene backbone and $R^2$ is similar to $R^1$ described above, wherein a preferable group for $R^2$ is also similar to that of $R^1$.

It is possible to obtain a fullerene derivative dimer represented by formula (2) described above by a publicly known method (for example, a method described in S. Lu et al., Angew. Chem. Int. Ed. 51, 802-806 (2012)).

In formula (3) described above, $Ar^2$ is similar to $Ar^1$ described above, wherein a preferable group for $Ar^2$ is also similar to that of $Ar^1$.

Furthermore, it is preferable for at least one of $R^2$ and $Ar^2$ to contain an ester structure.

For a reaction as described above, it is sufficient to mix a fullerene derivative dimer represented by formula (2), an aromatic compound represented by formula (3), an alcohol, and a halogenating agent in solvent to cause a reaction.

A reaction temperature is preferably 0 to 100° C., more preferably 20 to 100° C., and even more preferably 40 to 100° C. Within this range, it is possible to obtain a fullerene derivative represented by formula (1) at a high yield that is excellent in a productivity thereof.

It is sufficient to conduct a reaction until a time at when a fullerene derivative represented by formula (1) is produced at a high yield while proceeding of the reaction is analyzed by means of a high performance liquid chromatography (HPLC), a thin layer chromatography (TLC), or the like. A reaction time capable of normally obtaining a fullerene derivative represented by formula (1) is preferably 5 minutes to 200 hours, more preferably 10 minutes to 100 hours, and even more preferably 30 minutes to 24 hours.

An alcohol described above is not particularly limited and it is possible to use, for example, methanol, ethanol, propanol, isopropanol, or butanol, wherein methanol is preferable from the viewpoint of a reaction yield.

A halogenating agent described above is not particularly limited and it is possible to provide, for example, a halogen such as iodine or bromine, an organic halide such as N-bromosuccinimide or N-iodosuccinimide, or the like, wherein it is preferable to use N-bromosuccinimide from the viewpoint of an excellent reaction yield.

A solvent described above is not particularly limited and it is possible to use, for example, 1,2-dichlorobenzene or the like. Furthermore, it is also possible to use, as a solvent, a compound represented by formula (3), an alcohol and/or a halogenating agent that is/are used for such a reaction.

Practical Examples

An embodiment of the present invention will specifically be described below, based on practical examples. Here, an embodiment of the present invention is not limited to these practical examples.

Practical Example 1

Synthesis of compound 4a

Anisole (0.54 mL, 5.0 mmol) was added to a mixture of fullerene derivative dimer 1a (87 mg, 0.05 mmol) obtained by a method described in S. Lu et al., Angew. Chem. Int. Ed. 51, 802-806 (2012), N-bromosuccinimide (that will be referred to as "NBS", below) (36 mg, 0.20 mmol), methanol (100 µL), and 1,2-dichlorobenzene (that will be referred to as "ODCB", below) (20 mL) at room temperature under air atmosphere, and subsequently, stirring was conducted at 70° C. for 6 hours to cause a reaction. Proceeding of the reaction was traced by means of high performance liquid chromatography (that will be referred to as "HPLC" below) and thin layer chromatography. After the reaction, a reaction mixture was directly purified by means of silica gel column chromatography (eluent: toluene). After a solvent was distilled away, an obtained solid was washed with methanol and dried to obtain compound 4a as a dark brown solid. A yield thereof was 73%.

Compound 4a: dark brown solid; dissolvable solvents: $CHCl_3$, toluene, ODCB; $^1$H NMR (400 MHz, $CDCl_3/CS_2$=1/4) δ 3.92 (3H, s), 3.97 (3H, s), 4.26 (1H, d, J=13.2 Hz), 4.32 (1H, d, J=13.2 Hz), 7.08 (2H, d, J=8.8 Hz), 7.35 (1H, dd, J=7.6 Hz, 7.6 Hz), 7.68 (1H, d, J=7.6 Hz), 7.84 (1H, d, J=7.6 Hz), 8.05 (1H, d, J=7.6 Hz), 8.11 (1H, s); $^{13}$C NMR (100 MHz, $CDCl_3/CS_2$=1/4) δ 47.79, 51.41, 54.74, 59.59, 114.62, 127.52, 127.89, 128.40, 129.9, 131.08, 132.48, 134.33, 135.43, 138.06, 141.91, 142.04, 142.17, 142.64, 142.77, 142.81, 143.57, 143.62, 143.64, 143.71, 143.91, 144.41, 146.49, 146.55, 146.59, 148.19, 148.26, 150.92, 158.98; HRMS (ESI, positive) C76H16O3Na [M+Na]+: 999.0992. found 999.0992.

A reaction of compound 3a with an anisole as a nucleophile under presence of NBS was further studied (see Table 1 and formula (4) described below).

Practical Example 2

Anisole (0.54 mL, 5.0 mmol) was added to a mixture of fullerene derivative dimer 1a (87 mg, 0.05 mmol) obtained by a method described in S. Lu et al., Angew. Chem. Int. Ed. 51, 802-806 (2012), NBS (20 mg, 0.11 mmol), methanol (100 µL), and ODCB (20 mL) at room temperature under air atmosphere, and subsequently, stirring was conducted at 50° C. for 20 hours to cause a reaction. A yield of each component after the reaction was calculated by means of HPLC using $C_{60}$ as an internal standard. The results are illustrated in Table 1. Compound 4a was a main product and was obtained at a yield of 55%. In addition, alkoxy-group-containing compound 3a (yield: 2%) and hydroxyl-group-containing compound 2a (yield: 3%) were obtained.

Compound 3a: dark brown solid; dissolvable solvents: $CHCl_3$, toluene, ODCB; $^1$H NMR (400 MHz, $CDCl_3/CS_2$=1/4) δ 3.94 (3H, s), 4.07 (3H, s), 4.37 (1H, d, J=12.8 Hz), 4.43 (1H, d, J=12.8 Hz), 7.54 (1H, dd, J=7.6 Hz, 7.6 Hz), 7.80 (1H, d, J=7.6 Hz), 8.05 (1H, d, J=7.6 Hz), 8.22 (1H, s); $^{13}$C NMR (100 MHz, $CDCl_3/CS_2$=1/4) δ 48.43, 51.61, 54.03, 59.31, 80.72, 127.20, 128.11, 128.46, 130.08, 130.13, 131.4, 134.76, 135.43, 138.24, 139.37, 139.56, 140.40, 141.07, 141.68, 141.84, 142.15, 142.17, 142.2, 142.48, 142.51, 142.53, 142.63, 142.8, 142.84, 142.86, 142.91, 143.00, 143.34, 143.55, 143.60, 143.63, 143.80, 143.81, 143.85, 144.05, 144.12, 144.49, 144.63, 145.14, 145.31, 145.95, 146.16, 146.29, 146.44, 146.54, 146.58, 146.71, 146.80, 146.87, 147.22, 148.01, 148.49, 149.03, 153.01, 153.98, 165.65; HRMS (ESI, positive) C70H12O3 [M+Na]+: 923.0679. found 923.0672.

Comparative Example 1

Reaction was caused similarly to Practical Example 2 except that N,N-dimethylformamide (that will be referred to as "DMF", below) was used instead of methanol. The results are illustrated in Table 1. Compound 4a could not be obtained and compound 2a was obtained at a yield of 41% as a main product.

TABLE 1

|  | Co-solvent | Reaction time (h) | 4a Yield (%) | 3a yield (%) | 2a Yield (%) | 1a yield (%) |
|---|---|---|---|---|---|---|
| Practical Example 2 | MeOH | 20 | 55 | 2 | 3 | 12 |
| Comparative Example 1 | DMF | 20 | Trace | 0 | 41 | 18 |

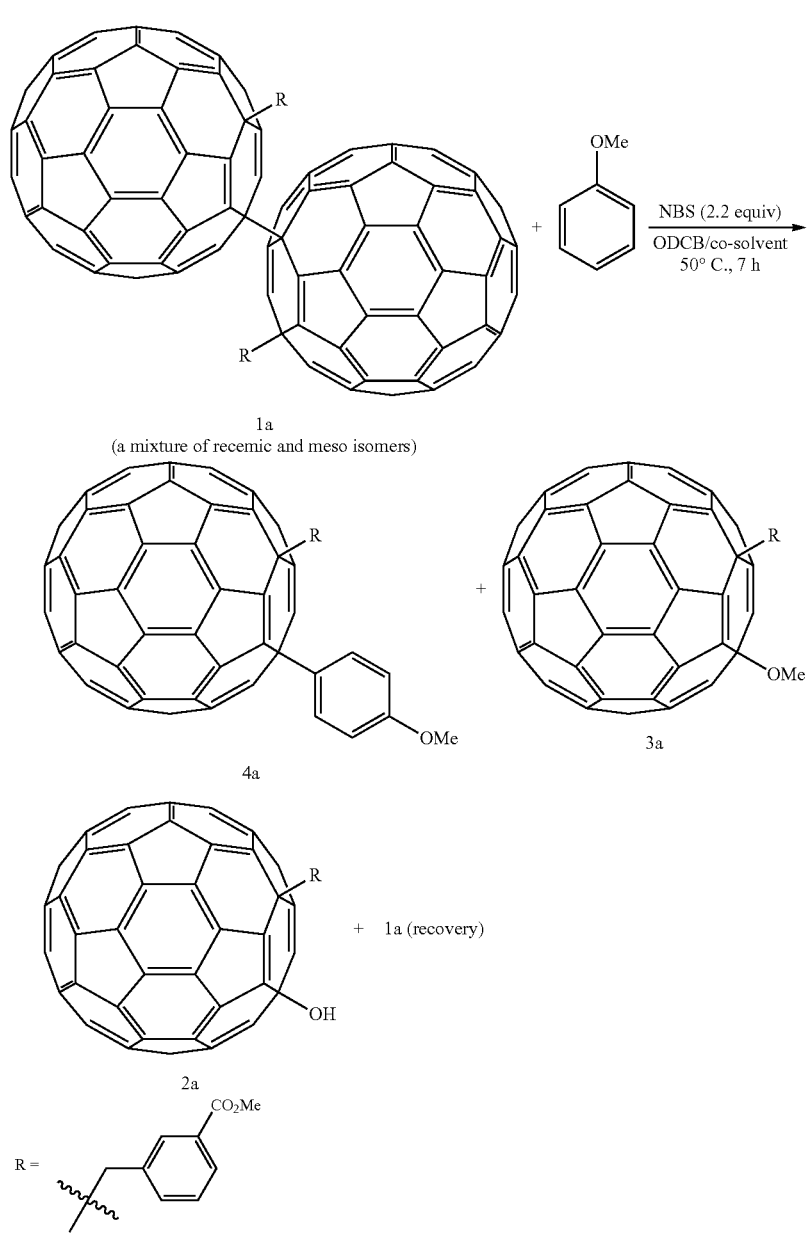

(4)

1a
(a mixture of recemic and meso isomers)

4a

3a

+ 1a (recovery)

2a

R =

Then, the cases where various kinds of nucleophiles were used instead of anisole in this reaction were studied (see Table 2 and formula (5)).

Practical Examples 3-8

Reaction was caused similarly to Practical Example 1 except that compound 1a or compound 1e (that was each obtained by a method described in S. Lu et al., Angew. Chem. Int. Ed. 51, 802-806 (2012)) was used as a raw material fullerene derivative dimer and compounds illustrated in Table 2 were used as nucleophiles instead of anisole. The results are also illustrated in Table 2. Compounds 4b-4g described below were obtained at good yields.

Compound 4b: dark brown solid; $^1$H NMR (400 MHz, CDCl$_3$/CS$_2$=1/4) δ 3.93 (3H, s), 3.97 (3H, s), 4.01 (3H, s), 4.14 (3H, s), 4.22 (1H, d, J=12.8 Hz), 4.27 (1H, d, J=12.8 Hz), 6.76 (1H, d, J=8.8 Hz), 7.36 (1H, dd, J=7.6, 7.6 Hz), 7.60 (1H, d, J=8.8 Hz), 7.69 (1H, d, J=7.2 Hz), 7.84 (1H, d, J=7.6 Hz), 8.2 (1H, s); $^{13}$C NMR (100 MHz, CDCl$_3$/CS$_2$=1/4) δ 47.44, 51.47, 55.36, 59.38, 60.01, 60.27, 106.9, 122.83, 127.79, 128.28, 129.9, 131.22, 134.36, 135.69, 137.9, 138.03, 138.11, 138.24, 140.32, 141.35, 141.63, 141.73, 142.09, 142.25, 142.29, 142.45, 142.63, 142.69, 142.72, 142.73, 142.84, 143.28, 143.38, 143.41, 143.55, 143.61, 143.66, 143.85, 143.87, 143.91, 144.04, 144.13, 144.16, 144.26, 144.49, 144.65, 144.77, 145.02, 145.05, 145.5, 146.36, 146.44, 146.49, 146.52, 146.57, 146.7, 146.77, 146.8, 148.07, 148.11, 148.15, 149.97, 152.7, 153.7, 155.63, 156.03, 165.31; HRMS (ESI, positive) C78H20O5Na [M+Na]+: 1059.1203. found 1059.1200.

Compound 4c: dark brown solid: dissolvable solvents: CHCl$_3$, toluene, ODCB; $^1$H NMR (400 MHz, CDCl$_3$/CS$_2$=1/4) δ 3.92 (3H, s), 4.38 (1H, d, J=12.8 Hz), 4.51 (1H, d, J=12.8 Hz), 7.25-7.27 (1H, m), 7.43 (1H, dd, J=7.6, 8.0 Hz), 7.52-7.53 (1H, m), 7.68-7.69 (1H, m), 7.79 (1H, d, J=7.6 Hz), 7.95 (1H, d, J=7.6 Hz), 8.20 (1H, s); $^{13}$C NMR (100 MHz, CDCl$_3$/CS$_2$=1/4) δ 48.00, 51.40, 56.85, 59.48, 125.39, 125.42, 127.49, 127.92, 128.44, 129.98, 131.20, 134.43, 135.37, 136.64, 137.92, 138.17, 138.71, 140.59, 141.53, 141.66, 141.82, 141.94, 142.07, 142.11, 142.23, 142.26, 142.69, 142.71, 142.73, 142.8, 143.29, 143.38, 143.44, 143.58, 143.71, 143.75, 143.81, 143.83, 143.89, 143.96, 143.98, 143.99, 144.03, 144.22, 144.37, 144.69, 144.79, 145.12, 145.15, 145.51, 145.92, 146.45, 146.55, 146.66, 146.68, 146.76, 147.51, 147.95, 148.2, 148.25, 150.05, 150.45, 155.12, 155.47, 165.08; HRMS (ESI, positive) C73H12O2SNa [M+Na]+: 975.0450. found 975.0450.

Compound 4d: $^{13}$C NMR (100 MHz, CDCl$_3$/CS$_2$=1/4) δ 8.19, 14.33, 22.97, 22.98, 29.06, 29.31, 29.42, 29.53, 30.88, 30.92, 31.82, 31.88, 48.08, 51.4, 59.42, 125.64, 127.12, 127.71, 127.97, 128.36, 129.05, 129.97, 131.27, 134.43, 135.43, 136.92, 137.98, 138.32, 138.71, 140.61, 141.67, 141.82, 141.98, 142.05, 142.13, 142.26, 142.59, 142.69, 142.74, 142.91, 143.29, 143.43, 143.47, 143.62, 143.68, 143.82, 143.85, 143.91, 144, 144.06, 144.42, 144.71, 144.87, 145.15, 145.58, 146.15, 146.5, 146.58, 146.73, 148.28, 150.4, 155, 155.12, 165.15.

Compound 4e: dark brown solid; dissolvable solvents: CHCl$_3$, toluene, ODCB; $^1$H NMR (400 MHz, CDCl$_3$/CS$_2$=1/4) δ 3.84 (3H, s), 3.94 (3H, s), 3.95 (3H, s), 4.35 (1H, d, J=12.4 Hz), 4.39 (1H, d, J=12.4 Hz), 7.10 (2H, d, J=8.4 Hz), 7.45-7.49 (2H, m), 7.55 (1H, d, J=7.6 Hz), 8.12 (2H, d, J=8.8 Hz); $^{13}$C NMR (100 MHz, CDCl$_3$/CS$_2$=1/4) δ 42.06, 51.91, 55.10, 55.18, 59.55, 60.93, 111.61, 114.66, 121.95, 127.81, 129.43, 130.51, 131.93, 133.27, 136.39, 137.56, 140.59, 142.11, 142.32, 142.43, 142.50, 142.86, 142.96, 143.56, 143.69, 143.77, 143.86, 143.90, 143.99, 144.09, 144.17, 144.21, 144.42, 144.75, 144.80, 145.27, 145.36, 145.97, 146.32, 146.32, 146.65, 146.68, 146.76, 146.82, 146.86, 148.18, 148.42, 148.61, 150.92, 157.49, 159.15, 165.08; HRMS (ESI, positive) C77H18O4Na [M+Na]$^+$: 1029.1097. found 1029.1098.

Compound 4f: dark brown solid; $^1$H NMR (400 MHz, CDCl$_3$/CS$_2$=1/4) δ 3.88 (3H, s), 3.91 (3H, s), 3.97 (3H, s), 4.10 (3H, s), 4.29 (1H, d, J=12.4 Hz), 4.33 (1H, d, J=12.0 Hz), 6.70 (1H, d, J=8.4 Hz), 7.43-7.45 (2H, m), 7.51 (1H, d, J=7.6 Hz), 7.58 (1H, dd, J=6.4, 8.0 Hz); $^{13}$C NMR (100 MHz, CDCl$_3$/CS$_2$=1/4) δ 41.49, 51.3, 54.77, 55.25, 59.1, 59.74, 60.04, 106.76, 111.42, 121.79, 122.83, 127.36, 129.18, 130.19, 131.57, 137.16, 137.64, 141.67, 141.75, 142.11, 142.16, 142.21, 142.24, 142.35, 142.57, 142.59, 142.69, 142.77, 143.33, 143.35, 143.37, 143.59, 143.69, 143.48, 143.89, 143.92, 143.94, 144.11, 144.24, 144.54, 144.56, 144.95, 144.97, 146.27, 146.39, 146.51, 146.53, 146.64, 146.69, 147.55, 148.01, 148.11, 148.22, 150.77, 152.56, 153.51, 156.25, 156.75, 157.09, 164.97; HRMS (ESI, positive) C79H22O6Na [M+Na]+: 1089.1309. found 1089.1309.

Compound 4g: dark brown solid; $^1$H NMR (400 MHz, CDCl$_3$/CS$_2$=1/4) δ 3.87 (3H, s), 3.94 (3H, s), 4.48 (1H, d, J=12.4 Hz), 4.55 (1H, d, J=12.8 Hz), 7.25-7.29 (1H, m), 7.52-7.55 (3H, m), 7.62 (1H, d, J=7.6 Hz), 7.73 (1H, s); $^{13}$C NMR (100 MHz, CDCl$_3$/CS$_2$=1/4) δ 42.05, 51.39, 54.67, 59.19, 111.42, 121.75, 125.27, 125.33, 127.31, 128.88, 130.59, 131.79, 136.66, 137.26, 137.83, 140.52, 141.54, 141.83, 142, 142.11, 142.16, 142.25, 142.72, 142.74, 142.77, 143.28, 143.38, 143.47, 143.49, 143.62, 143.76, 143.82, 143.85, 143.88, 143.94, 144.09, 144.16, 144.4, 144.51, 144.79, 145.04, 145.14, 146.01, 146.23, 146.43, 146.47, 146.49, 146.58, 146.65, 146.73, 147.57, 147.89, 149.14, 150.57, 156.26, 157.18, 165.09; HRMS (ESI, positive) C74H14O3SNa [M+Na]+: 1005.0556. found 1005.0556.

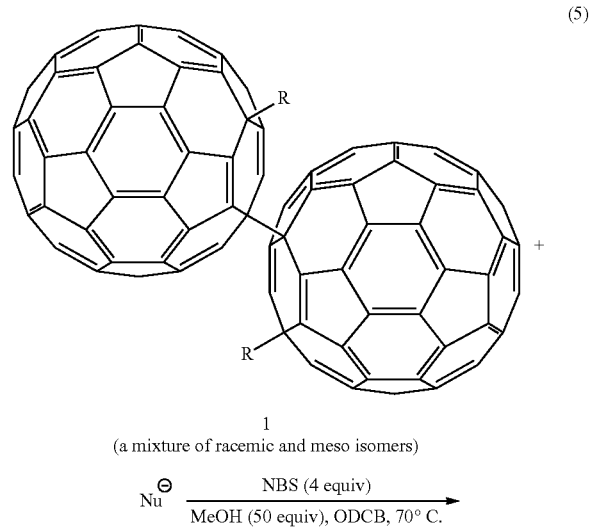

(5)

1
(a mixture of racemic and meso isomers)

$$\text{Nu}^\ominus \xrightarrow[\text{MeOH (50 equiv), ODCB, 70° C.}]{\text{NBS (4 equiv)}}$$

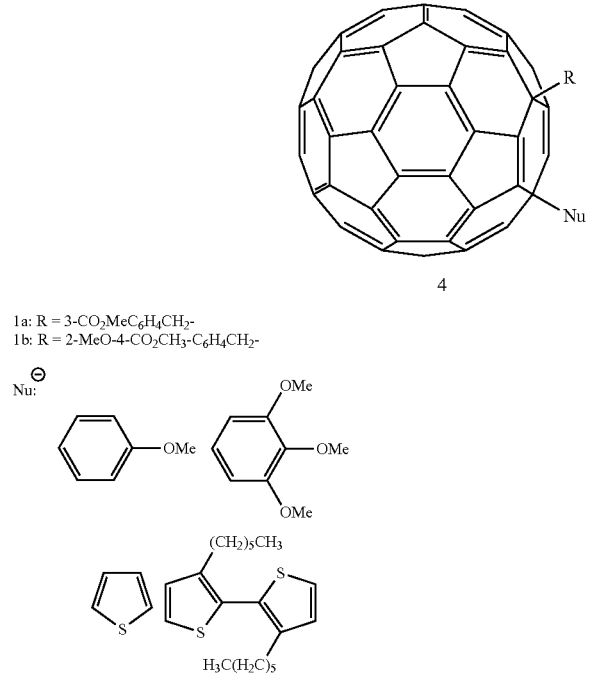

4

1a: R = 3-CO$_2$MeC$_6$H$_4$CH$_2$-
1b: R = 2-MeO-4-CO$_2$CH$_3$-C$_6$H$_4$CH$_2$-

Nu:

Chemical formulas of compounds 4b-4g are illustrated below.
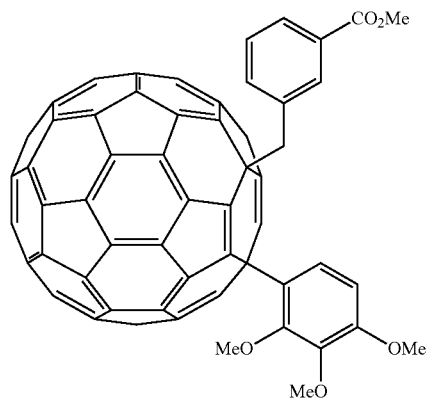
4b 83% (12 h)
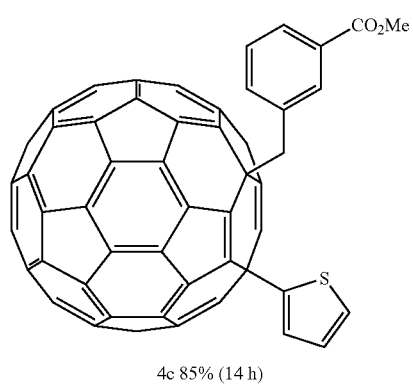
4c 85% (14 h)
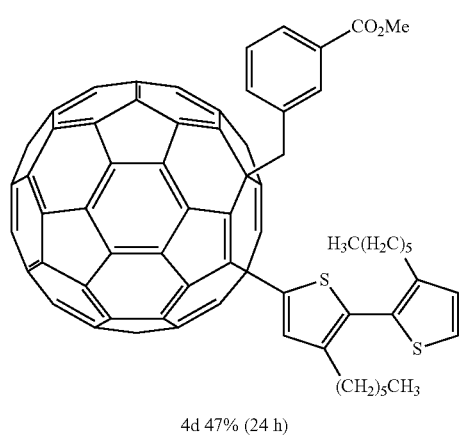
4d 47% (24 h)
-continued
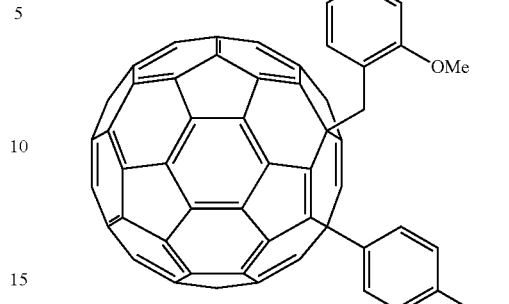
4e 40% (10 h)
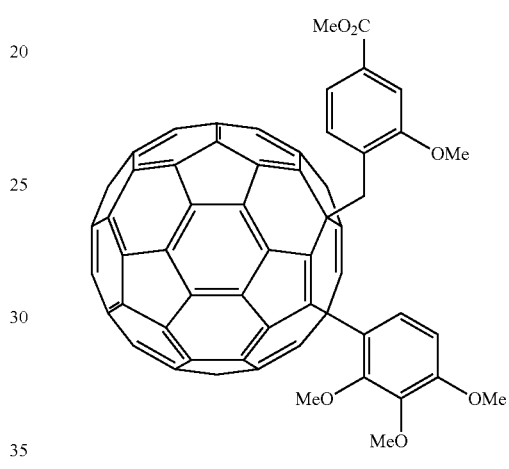
4f 70% (24 h)
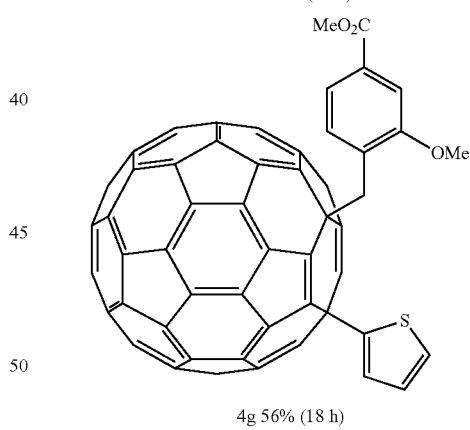
4g 56% (18 h)
TABLE 2
| | Dimer | Nucleophile | Reaction time (h) | Product/ Yield (%) |
|---|---|---|---|---|
| Practical Example 3 | 1a | 1,2,3-trimethoxybenzene | 12 | 4b/83 |
| Practical Example 4 | 1a | Thiophene | 14 | 4c/84 |
| Practical Example 5 | 1a | 3,3'-dihexyl-2,2'-bithiophene | 24 | 4d/47 |
| Practical Example 6 | 1e | Anisole | 10 | 4e/40 |

TABLE 2-continued

| | Dimer | Nucleophile | Reaction time (h) | Product/ Yield (%) |
|---|---|---|---|---|
| Practical Example 7 | 1e | 1,2,3-trimethoxybenzene | 24 | 4f/70 |
| Practical Example 8 | 1e | Thiophene | 18 | 4g/56 |

Practical Example 9

Reduction potentials of fullerene derivatives in the aforementioned practical examples were measured by means of cyclic voltammetry (that will be referred to as "CV" below). Values of electric potential with reference to a value of an Fc/Fc+ redox couple are illustrated in Table 3.

<CV Measurement Conditions>
Auxiliary electrolyte: 0.1M $Bu_4N^+PF_6^-$ in ODCB
Temperature: 25 degrees
Scanning speed: 0.02 V/s
Electrodes: glassy carbon (working electrode), platinum wire (counter electrode), Ag/Ag+ electrode (reference electrode)

Energy levels of lowest unoccupied molecular orbitals (that will be referred to as "LUMO", below) of 1,4-adducts that were fullerene derivatives in the aforementioned practical examples were estimated from first reduction potentials ($E^1_{1/2}$) measured by means of CV. The energy levels of LUMO were calculated by using the following formula:

$$\text{Energy level of LUMO} = -(E^1_{1/2} + 4.8 - E^{Fc/Fc+})eV.$$

The results are illustrated in Table 3.

Each of 1,4-adducts in the aforementioned practical examples exhibited three quasi-reversible reduction waves similarly to [6,6]-phenyl-$C_{61}$-butyric acid methyl ester (that will be referred to as [60]PCBM, below). Compound 4b and Compound 4f that had an electron-donating group on a phenyl group exhibited energy levels of LUMO comparable to that of [60]PCBM (−3.59 eV). The other 1,4-adducts that had a bithiophene ring or a thiophene ring exhibited comparatively lower energy levels of LUMO. These results suggested that an electrochemical characteristic of a 1,4-adduct according to an embodiment of the present invention could be adjusted by adding various functional groups thereto.

TABLE 3

| Compound | $E^1_{1/2}$ (V) | $E^2_{1/2}$ (V) | $E^3_{1/2}$ (V) | LUMO (eV) |
|---|---|---|---|---|
| 4a | −0.52 | −0.97 | −1.47 | −3.64 |
| 4b | −0.57 | −1.00 | −1.55 | −3.59 |
| 4c | −0.49 | −0.96 | −1.46 | −3.67 |
| 4d | −0.50 | −0.93 | −1.39 | −3.66 |
| 4f | −0.57 | −1.00 | −1.52 | −3.59 |
| 4g | −0.50 | −0.95 | −1.46 | −3.66 |

APPENDIX

A Fullerene Derivative and a Method for Manufacturing a Fullerene Derivative

An illustrative embodiment of the present invention may relate to at least one of a fullerene derivative and a method for manufacturing a fullerene derivative.

One object of an illustrative embodiment of the present invention may be to provide a fullerene derivative with an alkyl group and an aryl group that are directly added to a fullerene backbone thereof, and a manufacturing method thereof.

Another object of an illustrative embodiment of the present invention may be to provide a fullerene derivative with an alkyl group and an aryl group that are directly added to a fullerene backbone thereof, wherein it is possible to synthesize the fullerene derivative on a mild condition rapidly, and a manufacturing method thereof. Additionally, an alkyl group or an aryl group that is directly added to a fullerene backbone thereof, as described above, may have a substituent unless otherwise noted.

An illustrative embodiment of the present invention may be at least one of Illustrative Embodiments (1) to (13) described below.

Illustrative Embodiment (1) is a fullerene derivative represented by the following formula (1):

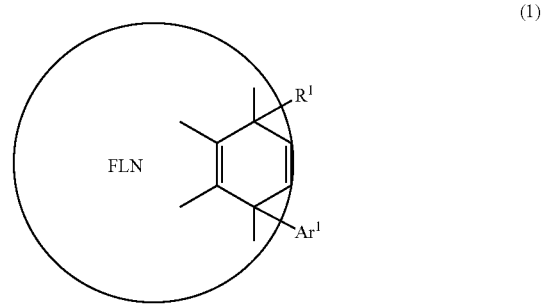

(1)

(In formula (1), FLN represents a fullerene backbone, $R^1$ represents a substituted or non-substituted alkyl group with a carbon number less than or equal to 24, and $Ar^1$ represents a substituted or non-substituted aryl group with a carbon number less than or equal to 24. Herein, the aryl group may be a heteroaryl group.).

Illustrative Embodiment (2) is the fullerene derivative as described in Illustrative Embodiment (1), wherein $R^1$ is a substituted or non-substituted aralkyl group with a carbon number less than or equal to 24.

Illustrative Embodiment (3) is the fullerene derivative as described in Illustrative Embodiment (1), wherein $Ar^1$ is selected from the group consisting of a phenyl group, 2-thienyl group, and a bithienyl group.

Illustrative Embodiment (4) is the fullerene derivative as described in Illustrative Embodiment (1), wherein at least one of $R^1$ and $Ar^1$ contains an ester structure.

Illustrative Embodiment (5) is the fullerene derivative as described in Illustrative Embodiment (1), wherein FLN is $C_{60}$.

Illustrative Embodiment (6) is a method for manufacturing a fullerene derivative, which includes a step of reacting a fullerene dimer represented by the following formula (2):

(2)

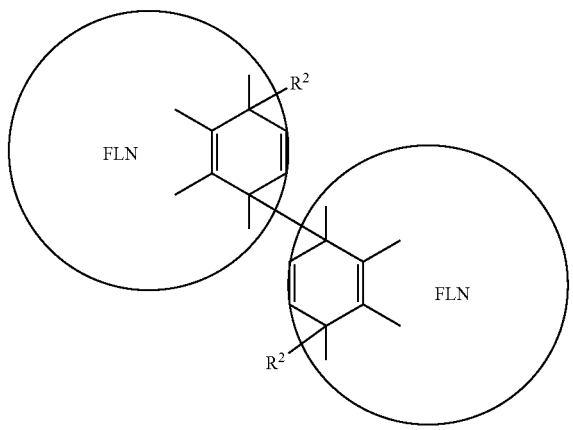

(In formula (2), FLN represents a fullerene backbone and $R^2$ represents a substituted or non-substituted alkyl group with a carbon number less than or equal to 24.) with an aromatic compound represented by the following formula (3):

$$H—Ar^2 \quad (3)$$

(In formula (3), $Ar^2$ represents a substituted or non-substituted aryl group with a carbon number less than or equal to 24. Herein, the aryl group may be a heteroaryl group.) under presence of an alcohol and a halogenating agent.

Illustrative Embodiment (7) is the method for manufacturing a fullerene derivative as described in Illustrative Embodiment (6), wherein $R^2$ is a substituted or non-substituted aralkyl group with a carbon number less than or equal to 24.

Illustrative Embodiment (8) is the method for manufacturing a fullerene derivative as described in Illustrative Embodiment (6), wherein $Ar^e$ is selected from the group consisting of a phenyl group, 2-thienyl group, and a bithienyl group.

Illustrative Embodiment (9) is the method for manufacturing a fullerene derivative as described in Illustrative Embodiment (6), wherein at least one of $R^2$ and $Ar^2$ contains an ester structure.

Illustrative Embodiment (10) is the method for manufacturing a fullerene derivative as described in Illustrative Embodiment (6), wherein the alcohol is selected from the group consisting of methanol, ethanol, propanol, isopropanol, and butanol.

Illustrative Embodiment (11) is the method for manufacturing a fullerene derivative as described in Illustrative Embodiment (6), wherein the halogenating agent is selected from the group consisting of bromine, N-bromosuccinimide, iodine, and N-iodosuccinimide.

Illustrative Embodiment (12) is the method for manufacturing a fullerene derivative as described in Illustrative Embodiment (6), wherein the step of reacting is conducted at a temperature of 0° C. to 100° C.

Illustrative Embodiment (13) is the method for manufacturing a fullerene derivative as described in Illustrative Embodiment (6), wherein the step of reacting is conducted for a time period of 5 minutes to 200 hours.

According to one illustrative embodiment of the present invention, it may be possible to provide a fullerene derivative with an alkyl group and an aryl group that are directly added to a fullerene backbone thereof, which is capable of being simply and inexpensively obtained on a mild condition by reacting an alkylated fullerene dimer with an alcohol, a specific halogenating agent, and an aromatic compound.

According to another illustrative embodiment of the present invention, it may be possible to provide a method for manufacturing a fullerene derivative wherein a fullerene derivative having a substituent that further contains an ester structure or the like therein is also synthesized readily.

According to another illustrative embodiment of the present invention, it may be possible to provide a photoelectric conversion element with an efficiency improved by using a fullerene derivative according to an illustrative embodiment of the present invention, because a fullerene derivative represented by the formula (1) described above is such that a control of a solubility in each kind of solvent and an electronic state is facilitated by introducing an alkyl group and an aryl group thereto and further it is also possible for such a substituent to contain an ester structure or the like so that a phase separation structure for a bulk hetero-junction structure is controlled.

According to another illustrative embodiment of the present invention, it may be possible to provide a fullerene derivative that is preferably used for a variety of applications such as an electronic material, a semiconductor body, a bioactive material, or the like.

Although the illustrative embodiment(s) and specific example(s) of the present invention have been described with reference to the accompanying drawing(s), the present invention is not limited to any of the illustrative embodiment(s) and specific example(s), and the illustrative embodiment(s) and specific example(s) may be altered, modified, or combined without changing the essence of or departing from the scope of the present invention.

What is claimed is:

1. A fullerene derivative represented by the following formula (1):

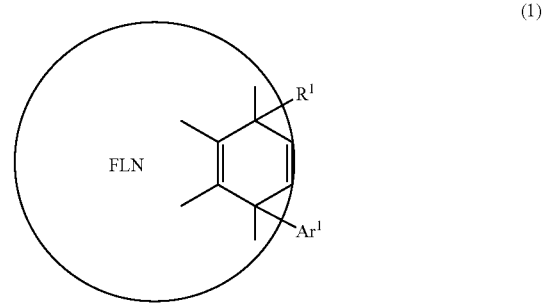

(1)

wherein FLN is a fullerene backbone, $R^1$ is a substituted or non-substituted aralkyl group with a carbon number ranging from 2 to 24, and $Ar^1$ is a substituted or non-substituted one selected from the group consisting of a phenyl group, 2-thienyl group, and a bithienyl group with a carbon number less than or equal to 24, wherein FLN is selected from the group consisting of $C_{60}$, $C_{70}$, $C_{76}$, $C_{78}$, $C_{82}$, $C_{84}$, $C_{90}$, $C_{94}$, $C_{96}$, $C_{120}$ and $C_{200}$, wherein when the $R^1$ is the substituted aralkyl group, the substituent of $R^1$ is selected from a group consisting of an aryl group, an alkoxy group, an ester-structure-containing group, a substituted or non-substituted amino group, an alkenyl group, an alkynyl group and a halogen atom, and wherein when the $Ar^1$ is the substituted one, the substituent of $Ar^1$ is selected from a group consisting of an alkyl group, an aryl group, an alkoxy group, an ester-structure-containing group, a substituted or non-substituted amino group, an alkenyl group, an alkynyl group and a halogen atom.

2. The fullerene derivative as claimed in claim 1, wherein at least one of $R^1$ and $Ar^1$ contains an ester structure.

3. The fullerene derivative as claimed in claim 1, wherein FLN is $C_{60}$.

4. A method for manufacturing a fullerene derivative, comprising:
a step of reacting a fullerene dimer represented by the following formula (2):

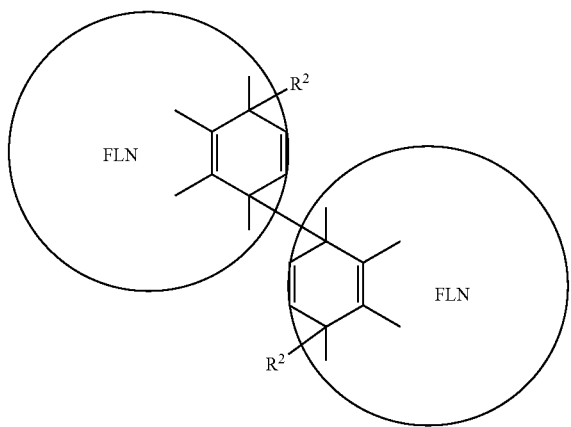

(2)

wherein FLN is a fullerene backbone selected from the group consisting of $C_{60}$, $C_{70}$, $C_{76}$, $C_{78}$, $C_{82}$, $C_{84}$, $C_{90}$, $C_{94}$, $C_{96}$, $C_{120}$ and $C_{200}$, and $R^2$ is a substituted or non-substituted aralkyl group with a carbon number less than or equal to 24, with an aromatic compound represented by the following formula (3):

(3)

wherein $Ar^2$ is a substituted or non-substituted one selected from the group consisting of a phenyl group, 2-thienyl group, and a bithienyl group with a carbon number less than or equal to 24, under presence of an alcohol and a halogenating agent,
wherein when the $R^2$ is the substituted aralkyl group, wherein the substituent of $R^2$ is selected from a group consisting of an aryl group, an alkoxy group, an ester-structure-containing group, a substituted or non-substituted amino group, an alkenyl group, an alkynyl group and a halogen atom, and
wherein when the $Ar^2$ is the substituted one, wherein the substituent of $Ar^2$ is selected from a group consisting of an alkyl group, an aryl group, an alkoxy group, an ester-structure-containing group, a substituted or non-substituted amino group, an alkenyl group, an alkynyl group and a halogen atom.

5. The method for manufacturing a fullerene derivative as claimed in claim 4, wherein at least one of $R^2$ and $Ar^2$ contains an ester structure.

6. The method for manufacturing a fullerene derivative as claimed in claim 4, wherein the alcohol is selected from the group consisting of methanol, ethanol, propanol, isopropanol, and butanol.

7. The method for manufacturing a fullerene derivative as claimed in claim 4, wherein the halogenating agent is selected from the group consisting of bromine, N-bromosuccinimide, iodine, and N-iodosuccinimide.

8. The method for manufacturing a fullerene derivative as claimed in claim 4, wherein the step of reacting is conducted at a temperature of 0° C. to 100° C.

9. The method for manufacturing a fullerene derivative as claimed in claim 4, wherein the step of reacting is conducted for a time period of 5 minutes to 200 hours.

10. The fullerene derivative as claimed in claim 1, wherein $R^1$ is selected from a group consisting of $3\text{-}CO_2CH_3C_6H_4CH_2\text{—}$ and $2\text{-}CH_3O\text{-}4\text{-}CO_2CH_3\text{—}C_6H_4CH_2\text{—}$.

11. The fullerene derivative as claimed in claim 1, wherein $Ar^1$ is selected from a group consisting of anisole, 1,2,3-trimethoxybenzene and thiophene, 3,3'-dihexyl-2,2'-bithiophene.

12. The fullerene derivative as claimed in claim 10, wherein $Ar^1$ is selected from a group consisting of anisole, 1,2,3-trimethoxybenzene and thiophene, 3,3'-dihexyl-2,2'-bithiophene.

13. The fullerene derivative as claimed in claim 1, wherein a combination of $R^1$ and $Ar^1$ is, (a) $3\text{-}CO_2CH_3C_6H_4CH_2\text{—}$ and anisole, (b) $3\text{-}CO_2CH_3C_6H_4CH_2\text{-}$ and 1,2,3-trimethoxybenzene, (c) $3\text{-}CO_2CH_3C_6H_4CH_2\text{—}$ and thiophene, (d) $3\text{-}CO_2CH_3C_6H_4CH_2\text{—}$ and 3,3'-dihexyl-2,2'-bithiophene, (e) $2\text{-}CH_3O\text{-}4\text{-}CO_2CH_3\text{—}C_6H_4CH_2\text{—}$ and anisole, (f) $2\text{-}CH_3O\text{-}4\text{-}CO_2CH_3\text{—}C_6H_4CH_2\text{—}$ and 1,2,3-trimethoxybenzene, or (g) $2\text{-}CH_3O\text{-}4\text{-}CO_2CH_3\text{—}C_6H_4CH_2\text{—}$ and thiophene.

14. The method for manufacturing a fullerene derivative as claimed in claim 4, wherein $R^2$ is selected from a group consisting of $3\text{-}CO_2CH_3C_6H_4CH_2\text{—}$ and $2\text{-}CH_3O\text{-}4\text{-}CO_2CH_3\text{—}C_6H_4CH_2\text{—}$.

15. The method for manufacturing a fullerene derivative as claimed in claim 4, wherein $Ar^2$ is selected from a group consisting of anisole, 1,2,3-trimethoxybenzene and thiophene, 3,3'-dihexyl-2,2'-bithiophene.

16. The method for manufacturing a fullerene derivative as claimed in claim 14, wherein $Ar^2$ is selected from a group consisting of anisole, 1,2,3-trimethoxybenzene and thiophene, 3,3'-dihexyl-2,2'-bithiophene.

17. The method for manufacturing a fullerene derivative as claimed in claim 4, wherein a combination of $R^2$ and $Ar^2$ is, (a) $3\text{-}CO_2CH_3C_6H_4CH_2\text{—}$ and anisole, (b) $3\text{-}CO_2CH_3C_6H_4CH_2\text{—}$ and 1,2,3-trimethoxybenzene, (c) $3\text{-}CO_2CH_3C_6H_4CH_2\text{—}$ and thiophene, (d) $3\text{-}CO_2CH_3C_6H_4CH_2\text{—}$ and 3,3'-dihexyl-2,2'-bithiophene, (e) $2\text{-}CH_3O\text{-}4\text{-}CO_2CH_3\text{—}C_6H_4CH_2\text{-}$ and anisole, $2\text{-}CH_3O\text{-}4\text{-}CO_2CH_3\text{—}C_6H_4CH_2\text{—}$ and 1,2,3-trimethoxybenzene, or (g) $2\text{-}CH_3O\text{-}4\text{-}CO_2CH_3\text{—}C_6H_4CH_2\text{—}$ and thiophene.

18. The fullerene derivative as claimed in claim 1,
wherein when $R^1$ is the substituted aralkyl group, the substituent of $R^1$ is selected from a group consisting of a phenyl group, a napthyl group, a methoxy group, an ethoxy group, a butoxy group, a methoxy carbonyl group, an acetyloxy group, a dimethyl amino group, a vinyl group and a halogen atom,
wherein when $Ar^1$ is the substituted one, the substituent of $Ar^1$ is selected from a group consisting of a methyl group, an ethyl group, a butyl group, a phenyl group, a napthyl group, a methoxy group, an ethoxy group, a butoxy group, a methoxy carbonyl group, an acetyloxy group, a dimethyl amino group, a vinyl group and a halogen atom.

19. The method for manufacturing a fullerene derivative as claimed in claim 4, wherein when $R^2$ is the substituted aralkyl group, the substituent of $R^2$ is selected from a group consisting of a phenyl group, a napthyl group, a methoxy group, an ethoxy group, a butoxy group, a methoxy carbonyl group, an acetyloxy group, a dimethyl amino group, a vinyl group and a halogen atom, wherein when $Ar^2$ is the substituted one, the substituent of $Ar^2$ is selected from a group consisting of a methyl group, an ethyl group, a butyl group, a phenyl group, a napthyl group, a methoxy group, an ethoxy group, a butoxy group, a methoxy carbonyl group, an acetyloxy group, a dimethyl amino group, a vinyl group and a halogen atom.

* * * * *